US012274636B2

(12) United States Patent
Jahanian et al.

(10) Patent No.: US 12,274,636 B2
(45) Date of Patent: Apr. 15, 2025

(54) DECOMPRESSION THERAPY TREATMENT SYSTEM

(71) Applicant: KCI Manufacturing Unlimited Company, Westmeath (IE)

(72) Inventors: Shervin Jahanian, San Antonio, TX (US); Richard Kazala, San Antonio, TX (US); Larry Tab Randolph, San Antonio, TX (US); Jonathan G. Rehbein, San Antonio, TX (US); Tyler H. Simmons, San Antonio, TX (US)

(73) Assignee: KCI Manufacturing Unlimited Company, Westmeath (IE)

( * ) Notice: Subject to any disclaimer, the term of this patent is extended or adjusted under 35 U.S.C. 154(b) by 285 days.

(21) Appl. No.: 17/081,243

(22) Filed: Oct. 27, 2020

(65) Prior Publication Data

US 2021/0128340 A1 May 6, 2021

Related U.S. Application Data

(60) Provisional application No. 62/929,215, filed on Nov. 1, 2019.

(51) Int. Cl.
*A61F 5/34* (2006.01)
*A61F 5/01* (2006.01)

(52) U.S. Cl.
CPC .............. *A61F 5/34* (2013.01); *A61F 5/0106* (2013.01); *A61F 5/0111* (2013.01)

(58) Field of Classification Search
CPC .. A61F 5/13; A61F 5/34; A61F 5/0106; A61F 5/0111; A61F 13/02; A61F 13/023;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Ophelia A Hawthorne
*Assistant Examiner* — Michael Milo

(57) ABSTRACT

A treatment system includes an dressing having a decompression layer and an occlusive layer that secures the dressing about a treatment site, and defines a treatment chamber within which the decompression layer is positioned. Operation of an air displacement device fluidly coupled to the chamber causes the decompression layer to compress away from the tissue site, resulting in a pulling force being imparted onto the treatment site. This decompression of the tissue site increases the perfusion of blood and other fluids, and advantageously may reduce swelling at the treatment site. To increase the degree of lifting of the treatment site, the decompression layer is advantageously constructed to exhibit a parallel plate effect during use of the treatment system. For example, the decompression layer is constructed having a center of stiffness located closer to an outwardly-facing surface of the decompression layer than a tissue-facing surface of the decompression layer.

24 Claims, 12 Drawing Sheets

(58) Field of Classification Search
CPC .............. A61F 13/0216; A61F 13/0223; A61F 13/0266; A61F 13/06; A61F 13/061; A61F 13/064; A61F 13/063; A61F 13/067; A61F 13/069; A61F 13/101; A61F 13/068; A61F 2013/00089; A61F 2013/00825
USPC ........................................................ 602/75
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,001,953 A | 1/1977 | Fugere et al. |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,625,896 A | 5/1997 | LaBarbera et al. |
| 5,636,643 A | 6/1997 | Argenta et al. |
| 5,645,081 A | 7/1997 | Argenta et al. |
| 5,910,125 A * | 6/1999 | Cummings ......... A61F 13/0213 206/440 |
| 6,056,713 A | 5/2000 | Hayashi |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0203452 A1 | 9/2005 | Weston et al. |
| 2008/0167593 A1 | 7/2008 | Fleischmann |
| 2009/0299257 A1 | 12/2009 | Long et al. |
| 2010/0159192 A1 | 6/2010 | Cotton |
| 2012/0046582 A1 | 2/2012 | Hopman et al. |
| 2014/0163491 A1 | 6/2014 | Schuessler et al. |
| 2014/0276288 A1* | 9/2014 | Randolph ............ A61H 9/0057 601/152 |
| 2015/0032035 A1* | 1/2015 | Banwell ................ A61H 9/005 601/6 |
| 2015/0057624 A1 | 2/2015 | Simmons et al. |
| 2015/0080788 A1 | 3/2015 | Blott et al. |

(56) References Cited

U.S. PATENT DOCUMENTS

| | | |
|---|---|---|
| 2016/0262942 A1 | 9/2016 | Riesinger |
| 2019/0117466 A1 | 4/2019 | Kazala, Jr. et al. |

FOREIGN PATENT DOCUMENTS

| | | | |
|---|---|---|---|
| AU | 755496 B2 | 12/2002 | |
| CA | 2005436 A1 | 6/1990 | |
| CA | 3060484 A1 | 12/2018 | |
| DE | 26 40 413 A1 | 3/1978 | |
| DE | 43 06 478 A1 | 9/1994 | |
| DE | 29 504 378 U1 | 9/1995 | |
| DE | 102005049466 A1 * | 4/2007 | ........... A47C 31/006 |
| DE | 102011054619 A1 * | 4/2013 | ........... B60N 2/5621 |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| EP | 3473218 A1 | 4/2019 | |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | WO-2005052235 A1 * | 6/2005 | ............ A61F 13/04 |
| WO | 2016188968 A1 | 12/2016 | |
| WO | 2018152127 A1 | 8/2018 | |
| WO | WO-2018229008 A1 * | 12/2018 | ....... A61F 13/00068 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al.; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ? uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

(56) References Cited

OTHER PUBLICATIONS

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
International Search Report and Written Opinion for Corresponding Application No. PCT/IB2020/060158, mailed Feb. 11, 2021.
International Search Report and Written Opinion for related application PCT/IB2020/060151, mailed Feb. 4, 2021.
Chinese Office Action for related application 2020800809607, dated May 31, 2023.
Office Action for related U.S. Appl. No. 17/772,479, dated Jun. 7, 2023.
Office Action for related U.S. Appl. No. 17/772,479, dated Dec. 15, 2023.
Japanese Office Action for related application 2022-524956, dated May 7, 2024.
Office Action for related U.S. Appl. No. 17/772,479, dated Jun. 21, 2024.
Japanese Office Action for related application 2022-524956, dated Oct. 8, 2024.

* cited by examiner

| Substrate | Performance Improvement (compared to reticulated foam) | Description | Materials Composition | Weight | Thickness (inch) | Yarn Description (body) # of filaments | Yarn Description (body) Denier per filament | Yarn Description (intermediate layer) # of filaments | Yarn Description (intermediate layer) Denier per filament |
|---|---|---|---|---|---|---|---|---|---|
| FIG. 6A | 10.49% | High density/stiffness upper layer and lower layer | 100% Polyester | 22.8 | 0.25 | 100 | 3.4 | | 209.1 |
| FIG. 6B | 7.69% | Low density/stiffness upper layer and lower layer | 100% Polyester | 10.2 | 0.17 | 158 | 1.5 | | 37.7 |
| FIG. 6C | 24.6% | High density/stiffness upper layer; Low density/stiffness lower layer | 100% Polyester | 8.4 | 0.12 | 36 | 2.4 | 1 (mono-filament) | 32.9 |
| FIG. 6D | -16.06% | Discontinuous high density/stiffness upper layer; Continuous low density/stiffness lower layer | 100% Polyester | 12.5 | 0.15 | 46 | 5.5 | | 107.9 |
| FIG. 6E | 51.23% | Multilayer | 100% Polyester (bonded with co-polyamide adhesive) | 33 | 0.42 | Combination of decompression layers of FIG. 6A and FIG. 6B | | | |

FIG. 7

DECOMPRESSION THERAPY TREATMENT SYSTEM

CROSS-REFERENCE TO RELATED APPLICATIONS

This application claims the benefit of priority to the U.S. Provisional Application No. 62/929,215, filed on Nov. 1, 2019, the complete disclosure of which is hereby incorporated herein by reference in its entirety.

BACKGROUND

Swelling associated with trauma or certain pathologies (e.g. lymphedema) may cause various medical complications. For example, swelling can cause discomfort and pain, may limit range of motion, or otherwise negatively impact patient quality of life. Swelling may also limit the ability of a medical provider to medically image, view, access underlying tissue, or may otherwise interfere in the treatment of a patient, and thus may pose an impediment to the healing and recovery of the patient. In certain circumstances, swelling may lead to even more severe consequences, such as, e.g., atrophy of surrounding muscle tissue.

It would be advantageous to provide a durable, reusable treatment system that could be easily applied to a tissue site and which could be washed (or otherwise sterilized) between uses, and which could reliably and repeatedly be operated to provide decompression therapy to increase blood perfusion and lymphatic flow at a tissue site to reduce swelling.

SUMMARY

According to one implementation of the present disclosure, an apparatus for applying a lifting force to a tissue site of a patient includes an occlusive layer, a decompression layer, and a connector. The occlusive layer is configured to be sealed to a patient around the tissue site to define a substantially air-tight chamber. The decompression layer is disposed within the chamber defined by the occlusive layer at a location proximate the tissue site. The decompression layer includes a compressible fabric defining one or more channels therethrough. The connector is provided along the occlusive layer and is configured to fluidly couple the chamber to a vacuum source. Upon operation of the vacuum source, the decompression layer is configured to compress in a direction away from the tissue site.

According to some embodiments, the occlusive layer extends at least 360° around an extremity (or other anatomical structure) defining the tissue site upon being sealed to a patient, and the decompression layer compresses in a radially outwards direction during operation of the vacuum source. In other embodiments, the occlusive layer extends less than 360° around an extremity (or other anatomical structure) defining the tissue site upon being sealed to a patient, and the decompression layer compresses in a upwards direction during operation of the vacuum source.

In some embodiments, the decompression layer is formed from a macro-mesh material (e.g., a macro-mesh fabric). The macro-mesh material optionally includes an upper layer, a lower layer, and a plurality of filaments extending between and connecting the upper layer and the lower layer. The filaments are optionally flexible, such that a distance between the upper layer and the lower layer prior to operation of the vacuum source is greater than a distance between the upper layer and the lower layer during operation of the vacuum source In various embodiments, the upper layer extends substantially continuously relative to the lower layer. The upper layer has at least one of a higher stiffness and a higher density than the lower layer.

The macro-mesh material further optionally includes a first intermediate layer disposed between the upper layer and the lower layer. The first intermediate layer has at least one of a higher stiffness and a higher density than the lower layer. In some embodiments the first intermediate layer is formed from the same material as the upper layer. A plurality of filaments extend between the first intermediate layer and at least one of the lower layer and the upper layer.

The macro-mesh material further optionally includes a second intermediate layer disposed between the upper layer and the first intermediate layer. The second intermediate layer has at least one of a lower stiffness and a lower density than the first intermediate layer.

In other embodiments, the macro-mesh material further optionally includes a second intermediate layer disposed between the lower layer and the first intermediate layer. The second intermediate layer has at least one of a lower stiffness and a lower density than the first intermediate layer. In various embodiments, the second intermediate layer is formed from the same material as the lower layer.

A center of mass of the decompression layer may be located at a height along the decompression layer that is closer to the upper surface of the decompression layer than to the lower surface of the decompression layer.

An optional interface layer is located below the lower surface of the decompression layer. The interface layer contacts the skin surrounding the tissue site upon sealing of the occlusive layer to the patient. The interface layer may comprise a non-woven breathable fabric. The interface layer may be a discrete structure provided separately from the decompression layer. The interface layer is optionally selectively releasably attached to at least one of the decompression layer and the occlusive layer. In some embodiments, the interface layer is attached to the decompression layer along a lower surface thereof.

In some embodiments, the occlusive layer and decompression layer are attached to one another to define an annular structure comprising at least a first open end. The annular structure is sized for attachment to one of a knee, ankle, leg, arm or hand of a patient. In some embodiments, the annular structure optionally defines a sleeve-like structure that further comprises a second open end.

According to one implementation of the present disclosure, an apparatus for increasing at least one of blood perfusion and lymphatic flow at a tissue site includes a circumferentially extending occlusive layer, a decompression layer, and a connector. The occlusive layer is configured to be sealed to a patient around the tissue site to define a substantially air-tight chamber. The decompression layer has a lower surface configured to be disposed proximate a tissue site within the chamber defined by the occlusive layer. The connector is configured to fluidly couple the chamber to a vacuum source. Upon operation of the vacuum source, the decompression layer is configured to compress in a direction away from the tissue site.

The occlusive layer optionally includes one of a boot-like or hand-like configuration. A shape and size of the decompression layer may be similar to the occlusive layer configuration. Alternatively, a size of the decompression layer is smaller than a size of the occlusive layer, such that the decompression layer is concentric relative to the occlusive layer. In some embodiments, the occlusive layer includes at least one of a zipper and a gusset.

In some embodiments, the decompression layer includes a first mesh layer vertically offset from a second mesh layer by a flexible layer. The first mesh layer is positioned opposite the occlusive layer and the second mesh layer is positioned opposite the tissue site. The second mesh layer may move radially outwards towards the first mesh layer during operation of the vacuum source. The first mesh layer may having a higher density than the second mesh layer.

According to one implementation of the present disclosure, a method for providing decompression therapy includes attaching a dressing proximate intact skin extending over a treatment site. The dressing includes an occlusive layer configured to define a substantially air-tight chamber between the skin of the patient and a lower surface of the occlusive layer, and a compressible decompression layer including a plurality of fluid channels extending therethrough. An air displacement device fluidly coupled to the chamber is operated to evacuate air from the chamber. The evacuation of air from the chamber causes the decompression layer to compress in a direction away from the tissue site. The compression of the decompression layer in a direction away from the tissue site is configured to pull the intact skin in a direction outward relative to the treatment site.

The decompression layer optionally includes a first mesh layer facing the occlusive layer and a second mesh layer facing the treatment site. The second layer is configured to move relative to the first layer in a direction opposite the treatment site upon the evacuation of air from the chamber. In some embodiments, first layer has at least one of a greater density and a greater stiffness than the second layer.

An optional interface layer may be attached proximate the intact skin extending over the treatment site. In some embodiments, the occlusive layer and decompression layer are attached to the skin of the patient after attaching the interface layer to the patient. The occlusive layer may be attached to the patient after attaching the decompression layer to the patient.

The treatment site is optionally a location corresponding to at least one of a broken bone in a limb, a sprained tissue and a strained tissue. The evacuation of air from the chamber reduces swelling at the treatment site from a first degree of swelling to a second degree of swelling. In some embodiments, the treatment site undergoes surgical treatment following the reduction of swelling at the treatment site from the first degree of swelling to a degree of swelling that is equal to, or less than, the second degree of swelling. The reduction of swelling from the first degree of swelling to the second degree of swelling occurs from 3 to 7 days following an initial operation of the air displacement device to evacuate air from the chamber.

BRIEF DESCRIPTION OF THE DRAWINGS

FIG. 7 is a table illustrating a comparison of the performance of the illustrative decompression layers of FIGS. 6A-6E to the performance of a reticulated foam-based decompression layer during use of a decompression treatment system according to an illustrative embodiment;

DETAILED DESCRIPTION OF ILLUSTRATIVE EMBODIMENTS

Figure 1:
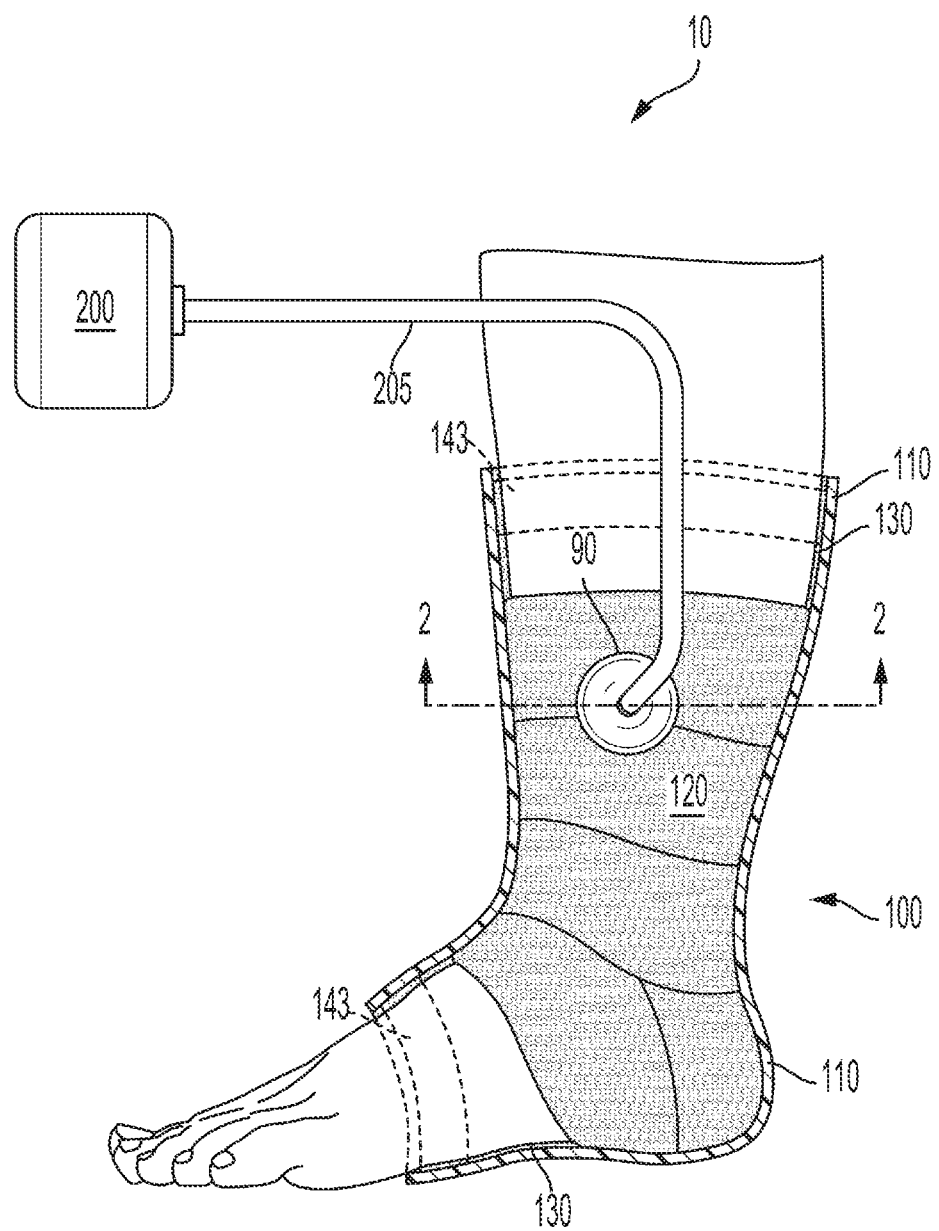
FIG. 1 is side view of a decompression treatment system showing a partial cross-sectional view of a dressing of the decompression treatment system, according to an illustrative embodiment.

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring generally to the FIGURES, a decompression therapy treatment system for applying a vacuum to intact skin extending over, or surrounding, different types of treatment tissue sites (such as, e.g., bone tissue, adipose tissue, muscle tissue, neural tissue, dermal tissue, vascular tissue, connective tissue, cartilage, tendons, ligaments, etc.) is described according to various embodiments. The application of vacuum to intact skin provided by the treatment system imparts a pulling (e.g., lifting) force to the intact skin, which decompresses the treatment tissue site and thereby increases the perfusion of blood and other fluids (e.g. lymphatic flow) at the treatment tissue site.

The decompression of the treatment tissue site resulting from the operation of the treatment system may advantageously be used to reduce swelling at a tissue site. The treatment system is configured for use in both medical and non-medical settings, and may be used to treat swelling occurring as a result of a variety of different conditions. For example, the treatment system may be used in a home setting by a patient to treat swelling resulting from an injury, over-exertion, an underlying medical condition (e.g., lymphedema), etc.

In yet other embodiments, the treatment system may also be used in a medical setting, such as, e.g., to reduce swelling during pre- and/or post-operative care of a patient. For example, reducing swelling at a treatment site (e.g., caused by a broken bone, edema, tissue sprain, tissue strain, etc.) prior to surgery may advantageously facilitate access to underlying tissue at a target surgical site, reduce surgery time and/or improve the outcome of surgical treatment. Use of a treatment system according to any of the embodiments described herein prior to surgical treatment may advantageously decrease the time needed to reduce swelling at the target surgical site to an acceptable degree of swelling as compared to the time that would be required to reduce swelling using conventional methods of treating swelling. For example, use of the treatment system may reduce swelling to an acceptable degree within 3 to 7 days of initiation of treatment using the treatment system.

In addition to the use of the treatment system to reduce swelling, the decompression therapy provided by the treatment system may advantageously also be used in the treatment of a variety of other medical conditions or ailments. As one non-limiting example, the treatment system may be used for the acute treatment of pain and/or inflammation (occurring, e.g., as a result of a sprain or other stress at a tissue site). In yet other situations, the treatment system may be used to increase blood perfusion and/or lymphatic flow at a treatment tissue site to minimize the effects of over-exertion (e.g., following athletic training or other intense activity).

Referring to FIG. 1, the treatment system 10 generally comprises a dressing 100 configured to be attached to a patient at a location surrounding a treatment tissue site, and an air displacement device 200 (e.g., vacuum source, negative pressure pump, etc.) configured to provide a source of negative pressure to a treatment chamber defined between the dressing 100 and the treatment tissue site. Upon operation of the air displacement device 200, the treatment chamber defined between the intact skin of the patient and the dressing 100 functions as a decompression chamber in which the skin and underlying tissue is subject to an outward pulling (e.g. lifting) force (representatively illustrated by the arrows in FIG. 2) as air is evacuated from the treatment chamber. An optional controller coupled to one or both of the dressing 100 and air displacement device 200 may control the application of decompression therapy to the treatment site using the treatment system 10.

Figure 11A:
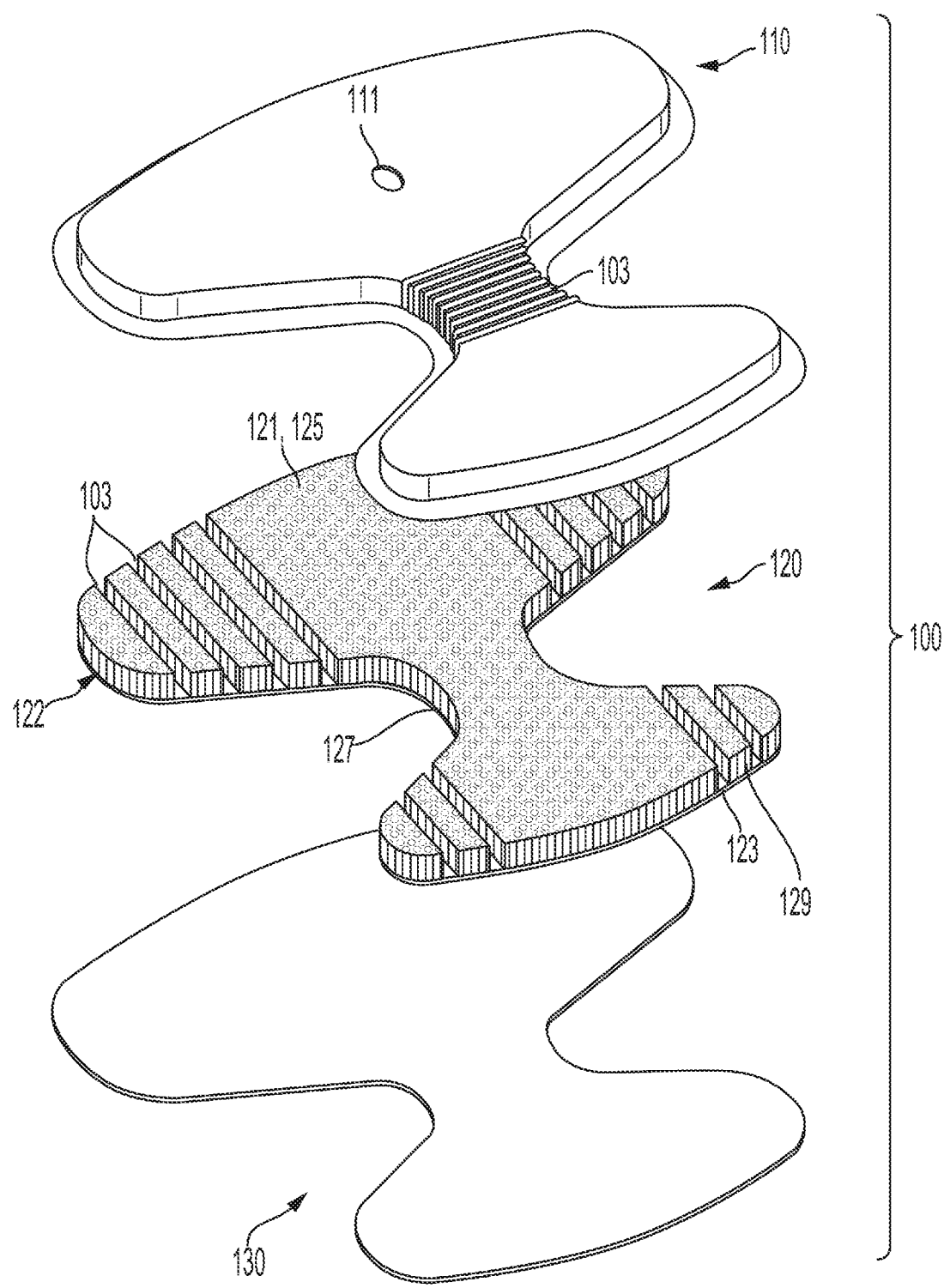
FIG. 11A is an exploded, perspective view of a dressing of a decompression treatment system, according to an illustrative embodiment.
Figure 11B:
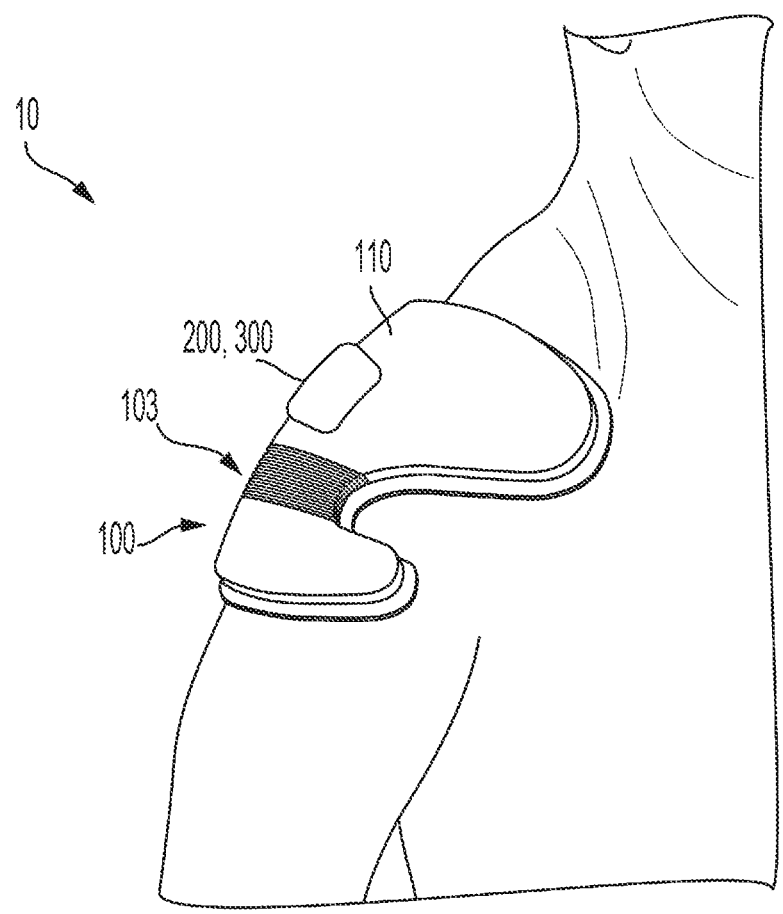
FIG. 11B is a perspective view of the dressing of FIG. 11A attached to a patient, according to an illustrative embodiment.

As illustrated by the treatment system 10 embodiment of FIG. 1, the dressing 100 and air displacement device 200 are optionally provided as discrete, separate components that are located remotely from one another. In such embodiments, the air displacement device 200 is fluidly and sealingly coupled to the treatment chamber via an external tubing 205. An optional connector port 90 sealingly attached around an opening 111 extending through the dressing 100 may facilitate the fluid connection between the treatment chamber and the air displacement device 200. In other embodiments (such as, e.g., embodiments in which the dressing 100 is configured to be wound around the patient) other connector port structures and/or configurations may be used to sealingly engage and fluidly couple the air displacement device 200 and the dressing 100. As shown in FIG. 11B, in yet other embodiments, the air displacement device 200 is optionally integrated into a module 300 that is fixedly, or removeably, attached to the dressing 100 to define an integral, self-contained, one-piece treatment system 10.

In addition to the use of the treatment system 10 as a standalone decompression therapy device, in various embodiments the treatment system 10 may be used in conjunction with (and may optionally be integrated into) one or more additional treatment systems. For example, although the treatment system 10 has been described as being used to impart a pulling force onto intact skin surrounding a treatment tissue site, in some embodiments, the treatment system 10 may be used to impart a pulling force onto a wound. In some such embodiments, the treatment system 10 is optionally applied atop (or integrated into) a wound dressing of a negative pressure wound therapy system ("NPWT" system). In yet other embodiments, the treatment system 10 may be used with a variety of other treatment systems, such as, e.g., a heat treatment system, systems configured to treat fractured bones, etc.

Dressing

Figure 3:
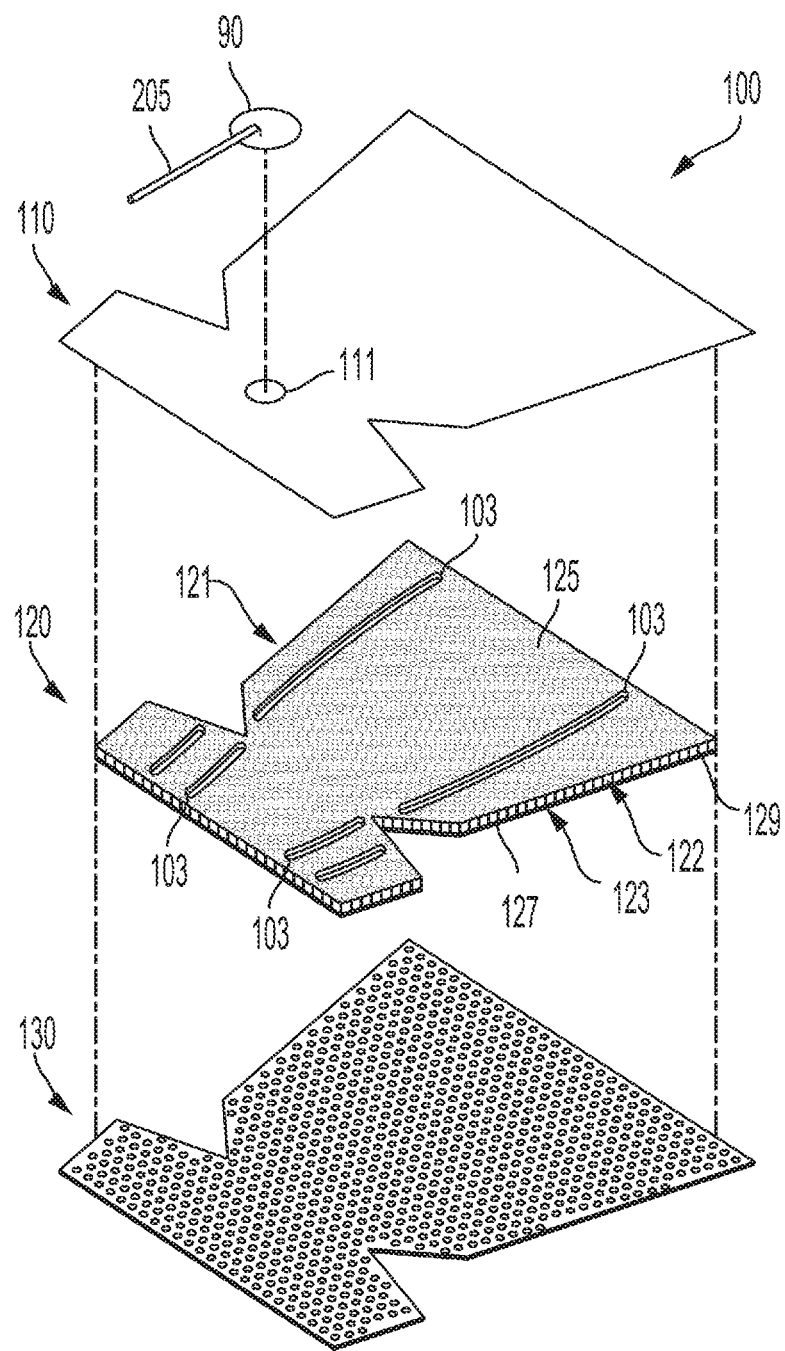
FIG. 3 is an exploded, perspective view of a dressing of a decompression treatment system, according to an illustrative embodiment.

Referring to FIG. 3, the dressing 100 generally includes a flexible occlusive layer 110 and a compressible decompression layer 120 (e.g., manifolding layer, macro-mesh layer, compressible layer, collapsible layer, etc.) comprising a plurality of flow channels extending therethrough. The occlusive layer 110 is configured to be attached to a patient (e.g., using an optional seal member) to define a treatment chamber surrounding the treatment tissue site. Upon attachment of the dressing 100 to a patient, the decompression layer 120 is arranged within the treatment chamber and extends along the treatment tissue site. An optional interface layer 130 extends between the skin of the patient and the decompression layer 120.

Figure 2:
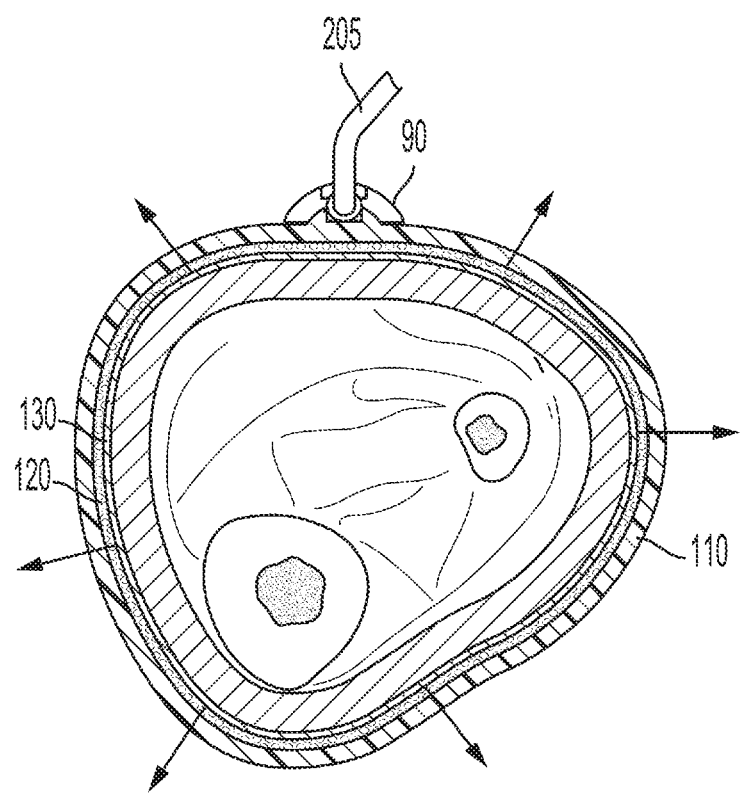
FIG. 2 is a cross-sectional view taken along line 2-2 of FIG. 1.

During operation of the treatment system 10, the evacuation of air from the treatment chamber occurring upon initiation of the air displacement device 200 causes the occlusive layer 110 and decompression layer 120 to be drawn towards the intact skin surrounding the treatment tissue site. Once the vacuum applied by the air displacement device 200 has removed most of the air from the treatment chamber, the continued application of negative pressure to the treatment chamber causes the compressible decompression layer 120 to collapse (e.g., compress) in on itself. This sustained application of negative pressure to the treatment chamber and collapse of the decompression layer 120 causes the intact skin at the treatment tissue site to be pulled outwardly (such as shown by the arrows of FIG. 2), thereby stimulating blood perfusion and lymphatic flow in the subcutaneous portions of the treatment tissue site.

A. Occlusive Layer

The occlusive layer 110 is configured to be sealed to the skin of a patient to envelop (e.g., surround, extend over, cover, etc.) the treatment tissue site. In some embodiments, such as, e.g., where the occlusive layer 110 is defined by a sleeve-like, boot-like, or other annular structure and/or by a sheet-like or tape-like structure configured to be wrapped about an anatomical structure, the occlusive layer 110 extends by approximately 360° (i.e. circumscribes) or more than 360° (i.e. the occlusive layer 110 wraps around upon itself) about a limb, extremity or other anatomical structure of the patient. In other embodiments (such as, e.g., during treatment of a knee, shoulder, elbow, etc.) the occlusive layer 110 is optionally defined by a sheet-like structure that extends less than 360° (e.g., less than 180°) around an anatomical structure of the patient.

Upon operation of the air displacement device 200, the sealed attachment between the occlusive layer 110 and the skin of the patient forms a sealed decompression treatment chamber via which negative pressure is transmitted to the treatment tissue site. An opening 111 is optionally defined through the occlusive layer 110, via which the treatment chamber is fluidly coupled to the air displacement device 200 of the treatment system 10. Alternatively, the treatment chamber is fluidly coupled to the vacuum source via a connector interposed between the skin of the patient and a lower surface of the occlusive layer 110.

The occlusive layer 110 may be formed from a variety of materials that are capable of maintaining a desired vacuum within the treatment chamber during use of the treatment system 10. The occlusive layer 110 is optionally formed from a material having a high MVTR, to allow moisture (e.g. perspiration) to be evaporated from the treatment tissue site during use of the treatment system 10. The material selected for the occlusive layer 110 is advantageously also sufficiently strong and resilient to allow the occlusive layer 110 to withstand extended periods of use of the treatment system 10. In embodiments in which the occlusive layer 110 is reusable, the material forming the occlusive layer 110 is optionally also sufficiently durable to allow the occlusive layer 110 to be cleaned (e.g. washed) between uses.

As shown in FIG. 3, in some embodiments the occlusive layer 110 is provided as a discrete and separate component of the dressing 100 which is integrated with the other components (e.g., decompression layer 120, interface layer 130, etc.) during attachment of the dressing 100 to the patient. In some such embodiments, the occlusive layer 110 optionally is provided with an adhesive along a lower surface thereof. Such a peel-and-place arrangement (in which the occlusive layer 110 is integrated with a seal member) allows the dressing 100 to be quickly wrapped around (or otherwise attached to) an anatomical structure of a patient (e.g., a foot, leg, arm, etc.), enabling a quick attachment of the dressing 100 to a patient. Referring to the representative embodiments of FIGS. 8A, 9A and 10, in other embodiments, the occlusive layer 110 is alternatively removably, or fixedly, integrated with the decompression layer 120.

Non-limiting examples of materials that may be used for the occlusive layer 110 include: polyurethane film (e.g., ESTANE 5714F), other polymer films such as, but not limited to poly alkoxyalkyl acrylates and methacrylates (e.g., such as those described in Great Britain Patent Application No. 1280631A filed Nov. 22, 2002, the entire disclosure of which is incorporated by reference herein), laminated fabrics (e.g., polyurethane laminated fabric, expanded polytetrafluoroethylene laminated fabric, etc.), polymer-coated fabrics, fabrics made from various synthetic fibers, etc.

B. Decompression Layer

The decompression layer 120 (e.g., manifolding layer, macro-mesh layer, compressible layer, collapsible layer, etc.) is configured to impart a pulling, or lifting, force onto the skin at the treatment tissue site. The decompression layer 120 is formed from a material including (or defining) a plurality of flow channels (e.g. pathways, passageways, pores, etc.) therethrough. The flow channels of the decompression layer 120 allow for a sustained transmission (e.g., manifolding) of negative pressure to the treatment tissue site during operation of the treatment system 10. Some or all of the flow channels are optionally interconnected to improve the distribution of fluids (e.g. air) provided to or removed from the treatment tissue site. The decompression layer 120 is formed from a compressible material having a stiffness sufficient to provide airflow through the flow channels at negative pressures up to at least approximately 150 mmHg.

Referring to FIG. 2, as air is evacuated from the treatment chamber during operation of the treatment system 10, the greater stiffness of the skin/muscle/bone underlying the treatment tissue site relative to the stiffness of the dressing 100 causes the occlusive layer 110 to be drawn against an outwardly-facing surface 125 (e.g. an upper surface, an outer surface, a surface facing away from the tissue site, etc.) of the decompression layer 120, and also causes a tissue-facing surface 127 (e.g. a lower surface, an inner surface, etc.) of the decompression layer 120 to be drawn towards and against (directly, or indirectly via an optional interface layer 130) the skin at the treatment tissue site. Once air has substantially been evacuated from the treatment chamber, the continued application of a vacuum to the treatment chamber results in the collapse of the compressible decompression layer 120.

Figure 4A:
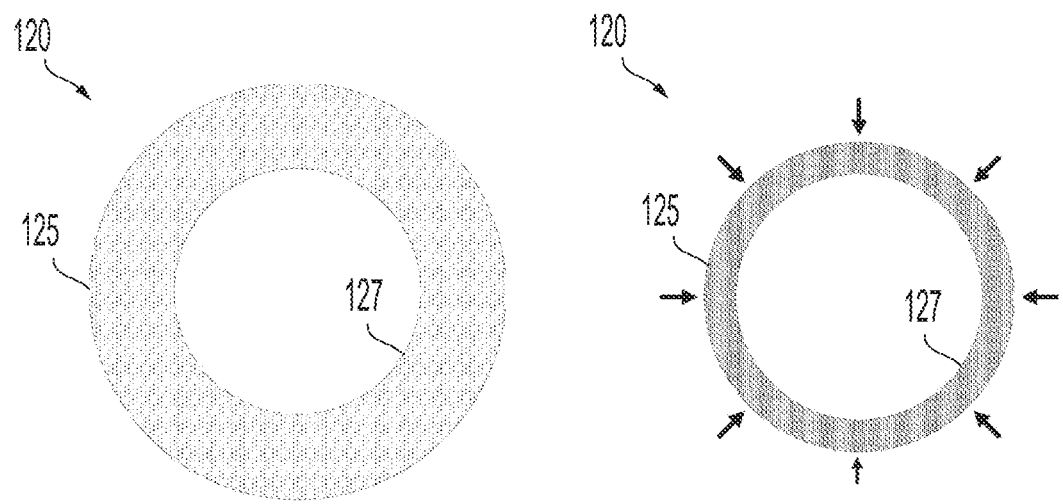
FIG. 4A is a schematic representation of the collapse of a decompression layer of a dressing of a decompression treatment system, according to an illustrative embodiment.

The direction (i.e. outward/inwards; upwards/downwards; away from/towards the tissue site; in a radial direction; in a vertical direction, etc.) in which the decompression layer 120 collapses (e.g., compresses) varies depending on the construction of the decompression layer 120. The collapse of a decompression layer 120 comprising a single layer, and formed from a material having a uniform density, in response to a vacuum is representatively illustrated in FIG. 4A. As shown by the arrows of FIG. 4A, such a decompression layer 120 having a center of stiffness that is located closer to the tissue-facing surface 127 than the outwardly-facing surface 125 of the decompression layer 120 will compress such that the outwardly-facing surface 125 of the decompression layer 120 is drawn towards the tissue-facing surface 127 of the decompression layer 120.

Figure 4B:
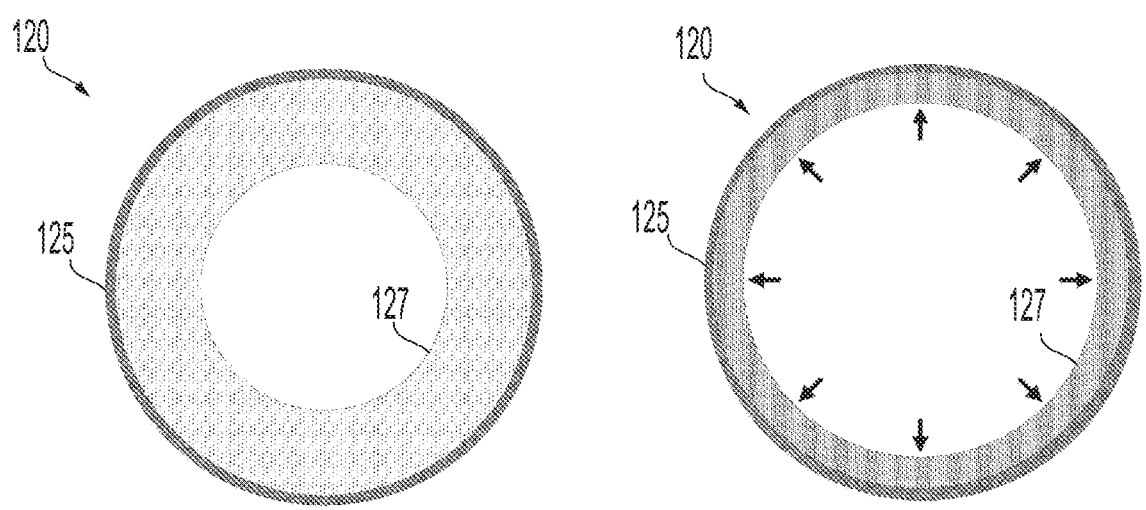
FIG. 4B is a schematic representation of the collapse of a decompression layer of a dressing of a decompression treatment system, according to an illustrative embodiment.

The collapse of a decompression layer 120 comprising an outer portion (i.e. a portion of the decompression layer 120 adjacent the outwardly-facing surface 125 that faces away from the tissue site) formed from a stiff material and an inner portion (i.e. a portion of the decompression layer 120 adjacent the tissue-facing surface 127) formed from a softer material in response to a vacuum is representatively illustrated in FIG. 4B. In contrast to the representative decompression layer 120 illustrated in FIG. 4A, a decompression layer 120 such as illustrated in FIG. 4B, which is defined by a center of stiffness that is located closer to the outwardly-facing surface 125 than the tissue-facing surface 127 of the decompression layer 120, will experience a parallel plate effect upon being subject to a vacuum during use of the treatment system 10. As illustrated by the arrows of FIG. 4B, this sandwiched arrangement of a softer, inner-half portion of the decompression layer 120 between two stiffer structures (i.e., the skin/muscle/bone underlying the treatment tissue site and a relatively harder, outer-half portion of the decompression layer 120) results in the tissue-facing surface 127 of the decompression layer 120 being drawn towards the outwardly-facing surface 125 of the decompression layer 120 as the decompression layer 120 collapses. The pulling force imparted onto the skin at the treatment tissue site as a result of such an outwardly directed collapse of the decompression layer 120 is effective for enhancing lymphatic flow and blood perfusion at the treatment tissue site.

Given the impact of the parallel plate effect on lymphatic flow and blood perfusion at a tissue site, the decompression layer 120 is advantageously constructed such that the center of stiffness of the decompression layer 120 is located closer to the outwardly-facing surface 125 than the tissue-facing surface 127 of the decompression layer 120). The decompression layer 120 is also advantageously constructed from a material that is sufficiently flexible to allow the decompression layer 120 to be secured to a patient and to allow for a range of motion of the body part to which the dressing 100 is attached during use of the treatment system 10.

The decompression layer 120 is advantageously also formed having sufficient structural integrity and resilience to withstand repeated applications of negative pressure thereto over the course of operation of the treatment system 10 (e.g., for periods of up to, or greater than, one week). To facilitate the reuse of the treatment system 10 with the same, or other, patients, the decompression layer 120 is additionally optionally constructed having a durability that allows the decompression layer 120 to be washed in-between uses.

Figure 5:
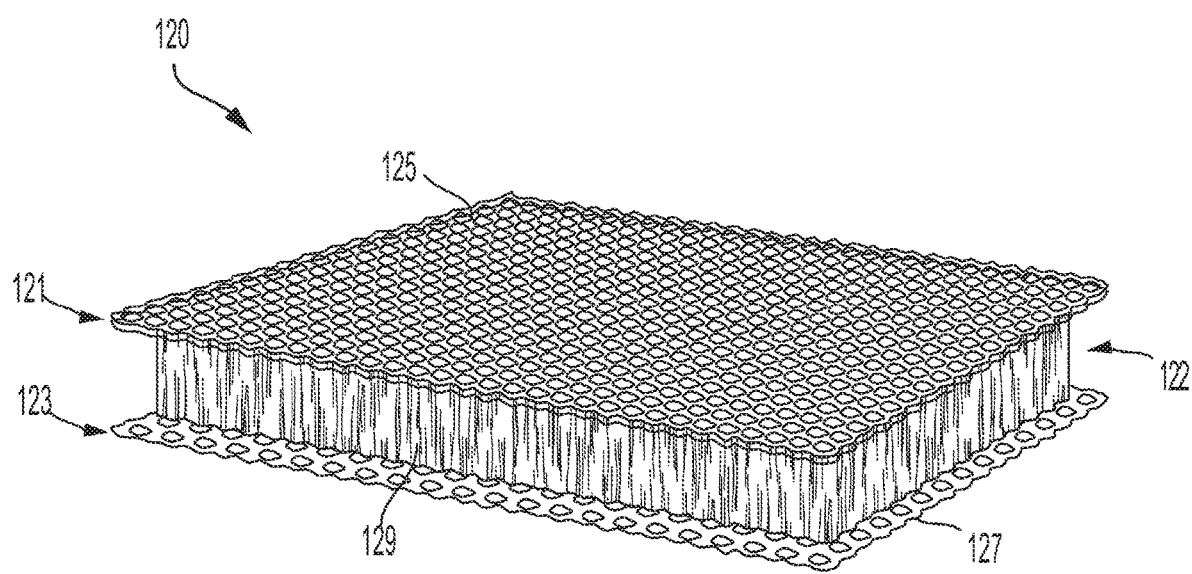
FIG. 5 is a perspective view of a material forming the decompression layer of a dressing of a decompression treatment system, according to an illustrative embodiment.

Referring to FIG. 5, a flexible, resilient and durable decompression layer 120 construction configured to impart an increased pulling force on skin at a tissue treatment site is shown according to an exemplary embodiment. In the decompression layer 120 embodiment of FIG. 5, the decompression layer 120 is defined by a macro-mesh material comprising a lower layer 123, an upper layer 121, and an intermediate layer 122. Upon integration of the decompression layer 120 into the tissue treatment system 10, a lower surface of the lower layer 123 defines the tissue-facing surface 127 (e.g., a lower surface, an inner surface, a radially inwardly extending surface, etc.) of the decompression layer 120, and an upper surface of the upper layer 121 defines the outwardly-facing surface 125 (e.g. an upper surface, an outer surface, a radially outwardly extending surface, etc.) of the decompression layer 120. The upper layer 121 and lower layer 123 are vertically offset from one another, as well as interconnected to one another, via the intermediate layer 122 (e.g., a connector layer).

The upper layer 121 and lower layer 123 defining the macro-mesh material forming the decompression layer 120 may be defined by a variety of different materials. To provide the decompression layer 120 with a desired degree of resilience and durability, one or both of the upper layer 121 and the lower layer 123 are formed from a textile material. The textile may be defined by a variety of different woven or non-woven patterns, weights, densities, fibers, stiffnesses, etc., depending on the desired properties of the decompression layer 120. According to various embodiments, one or both of the upper layer 121 and the lower layer 123 are formed from a polymer or nylon material (e.g., a polymer or nylon mesh).

To provide the decompression layer 120 with the desired offset center of stiffness (i.e., a center of stiffness that is located closer to the outwardly-facing surface 125 of the decompression layer 120), the upper layer 121 is formed from a different material, has a different construction, or otherwise varies from the lower layer 123. For example, the upper layer 121 is formed from a material having a greater stiffness than the material used for the lower layer 123. The materials selected for the upper layer 121 and/or lower layer 123 may optionally include a coating (e.g., an anti-microbial coating, a hydrophobic coating, etc.), to provide the decompression layer 120 with additional desired features.

The intermediate layer 122 may be formed from a variety of different materials. As shown in FIG. 5, according to various embodiments, the intermediate layer 122 is formed of a plurality of durable, resilient, and flexible (e.g., collapsible, deflectable, bendable, compressible, etc.) filament fibers 129 that allow the decompression layer 120 to collapse (e.g., compress, or otherwise cause a distance between the upper layer 121 and lower layer 123 to be reduced) one or more times during use of the treatment system 10. The filament fibers 129 forming the intermediate layer 122 may be defined by a variety of yarn types (e.g. monofilament, multifilament, spun, etc.), diameters, lengths, materials, weights, denier, densities, stiffness, etc. The selection and arrangement of filament fibers 129 may be varied based on the desired characteristics of the manifold layer. For example, the length and density of the filament fibers 129 forming the intermediate layer 122 may be varied based on a desired stiffness of the decompression layer 120.

The effects of varying various properties of the dual-layered decompression layer 120 arrangement of FIG. 5 on the degree of pulling force imparted onto the skin during operation of the treatment system 10 are described with reference to FIGS. 6A-6F and FIG. 7. Non-limiting properties of the decompression layer 120 embodiments illustrated in FIGS. 6A-6E are provided in the table of FIG. 7.

In general, a decompression layer 120 comprising a macro-mesh configuration such as, e.g., representatively illustrated by the embodiment of FIG. 5, is defined by a greater stiffness than a decompression layer 120 formed of single layer, uniformly dense, reticulated foam material. Accordingly, as illustrated by the table of FIG. 7—even if the dual-layered decompression layer 120 is defined by a center of stiffness located at (or substantially at) a center of the decompression layer 120 (such as, e.g., illustrated by the embodiments of FIGS. 6A and 6B)—the structure of the dual-layer decompression layer 120 provides enhanced blood perfusion and lymphatic flow at a treatment tissue site as compared to a decompression layer formed of a single layer, uniformly dense, reticulated foam material.

Figure 6A:
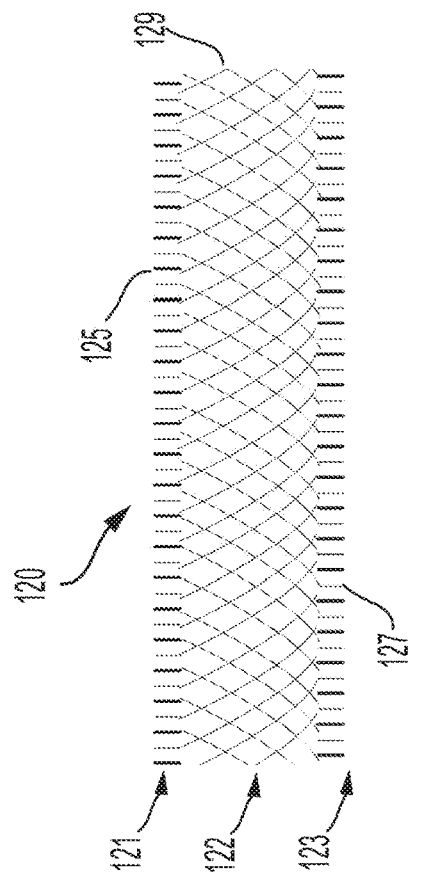
FIGS. 6A-6F are cross-sectional view of decompression layers, according to illustrative embodiments.

For example, as shown in the table of FIG. 7, in one embodiment, a decompression layer 120 embodiment such as shown in FIG. 6A which comprises a macro-mesh configuration having a high-density and/or high-stiffness (e.g., formed of a polyester material having a denier of approximately 3.4) upper layer 121 and lower layer 123, may increase the degree of perfusion and flow at the treatment tissue site by approximately 10.5% as compared to a decompression layer formed of a single layer, uniformly dense, reticulated foam material. As also shown in the table of FIG. 7, in one embodiment, a decompression layer 120 embodiment such as shown in FIG. 6B which comprises a macro-mesh configuration having a low-density and/or low-stiffness (e.g., formed of a polyester material having a denier of approximately 1.5) upper layer 121 and lower layer 123, may increase the degree of perfusion and flow at the treatment tissue site by approximately 7.7% as compared to a decompression layer formed of a single layer, uniformly dense, reticulated foam material.

Figure 6B:
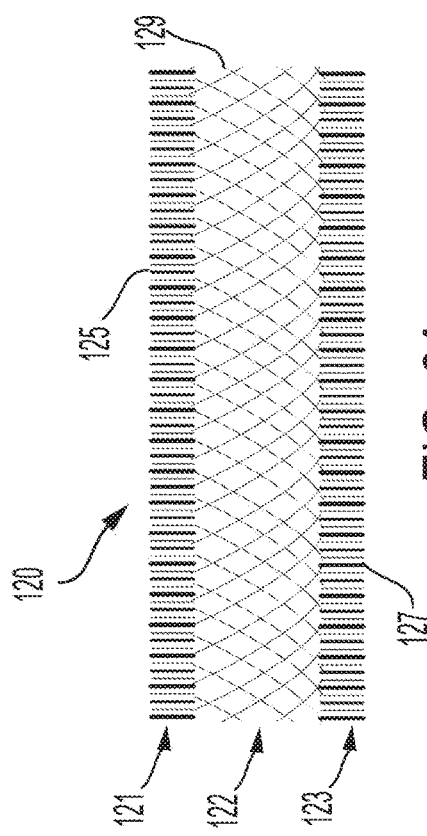

As illustrated by a comparison of the performance of the decompression layer 120 examples of FIGS. 6A and 6B as summarized in the table of FIG. 7, increasing the density (and stiffness) of the material used to form the substantially similar upper layer 121 and lower layer 123 of a decompression layer 120 such as e.g., illustrated by the embodiment of FIG. 6A will provide an increased pulling force as compared to a dual-layer decompression layer 120 embodiment having an upper layer 121 and lower layer 123 each formed from a lower density (and lower stiffness) material (such as, e.g., representatively illustrated by the embodiment of FIG. 6B).

Figure 6C:
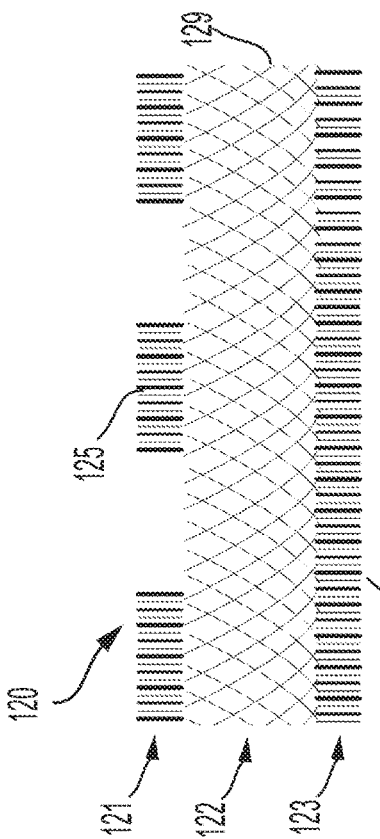

As illustrated by the table of FIG. 7, a dual-layer decompression layer 120 arrangement, such as representatively shown in FIG. 6C comprising an upper layer 121 formed from a higher density (and higher stiffness) material and a lower layer 123 formed from a lower density (and lower stiffness) material—which accordingly is defined by a center of stiffness located closer to the outwardly-facing surface 125 of the decompression layer 120—will impart an increased pulling force on the treatment tissue site as compared to a decompression layer 120 formed having both an upper layer 121 and a lower layer 123 formed from materials having the same density (and same stiffness), such as, e.g., the decompression layer embodiments of FIGS. 6A and 6B. For example, as compared to the 10.5% improvement over foam of the decompression layer 120 embodiment of FIG. 6A (which is formed from high density/stiffness upper layer 121 and lower layer 123) and the 7.7% improvement over foam of the decompression layer 120 embodiment of FIG. 6B (which is formed from low density/stiffness upper layer 121 and lower layer 123), a decompression layer embodiment having a high density and/or high stiffness upper layer 121 and a low density and/or low stiffness lower layer 123 (such as, e.g., the embodiment of FIG. 6C) exhibits an improvement of 24.6% in perfusion and flow as compared to a decompression layer formed of a single layer, uniformly dense, reticulated foam material.

Figure 6D:
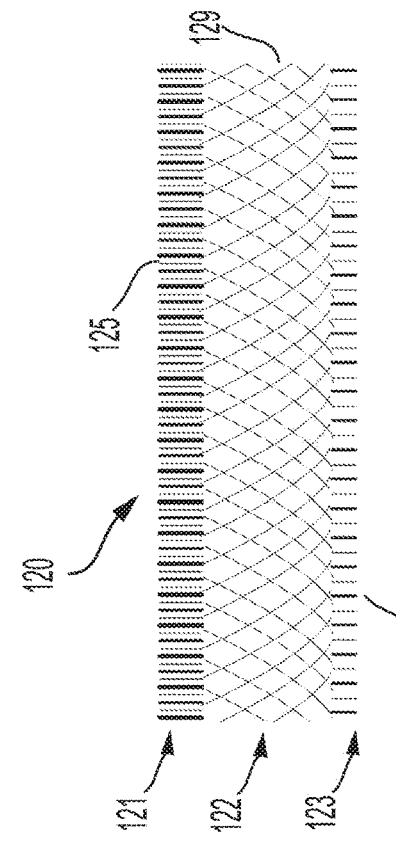

As illustrated by FIG. 7, the decompression layer 120 embodiment of FIG. 6D is formed from a high density (and high stiffness) material, and the lower layer 123 of the decompression layer 120 is also formed from a low density (and lower stiffness) material, similar to the materials used for the lower layer 123 and upper layer 121 of the decompression layer 120 embodiment of FIG. 6C. However, whereas the decompression layer 120 embodiment of FIG. 6C comprises a continuously extending upper layer 121, the upper layer 121 of the decompression layer 120 embodiment of FIG. 6D is instead defined by strips of the high density (and high stiffness) material that are separated from one another by portions of the intermediate layer 122 along which no upper layer 121 extends.

As a result of the interrupted upper layer 121 configuration of the decompression layer 120 embodiment of FIG. 6D, the center of stiffness of the decompression layer 120 of FIG. 6D is located closer to the tissue-facing surface 127 than to the outwardly-facing surface 125 of the decompression layer 120. As shown in FIG. 7, the effect of the center of stiffness of the decompression layer 120 of FIG. 6D being located closer to the tissue-facing surface 127 of the decompression layer 120 is that the decompression layer 120 embodiment of FIG. 6D imparts even less of a pulling force onto skin at the treatment tissue site than a uniformly dense, single layer reticulated foam-based decompression layer. Accordingly, as shown by the table of FIG. 7, a decompression layer arrangement such as that of FIG. 6D may result in a decrease in perfusion and flow at the treatment tissue site of 16.1% as compared to a decompression layer formed of a single layer, uniformly dense, reticulated foam material.

The degree of pulling force imparted onto the skin by the decompression layer 120 may be further augmented by constructing the decompression layer 120 to maximize the distance of the center of stiffness from the tissue-facing surface 127 of the decompression layer 120. As described with reference to FIG. 6C, one such option for maximizing this distance is to increase the stiffness of the upper layer 121 of the decompression layer 120 relative to the stiffness of the lower layer 123 of the decompression layer 120. As shown in FIG. 7, and illustrated by the embodiments of FIGS. 6E and 6F, an additional option for increasing the pulling force imparted onto skin during use of the treatment system 10 is to increase a thickness (i.e., distance between the outwardly-facing surface 125 and the tissue-facing surface 127) of the decompression layer 120.

Figure 6E:
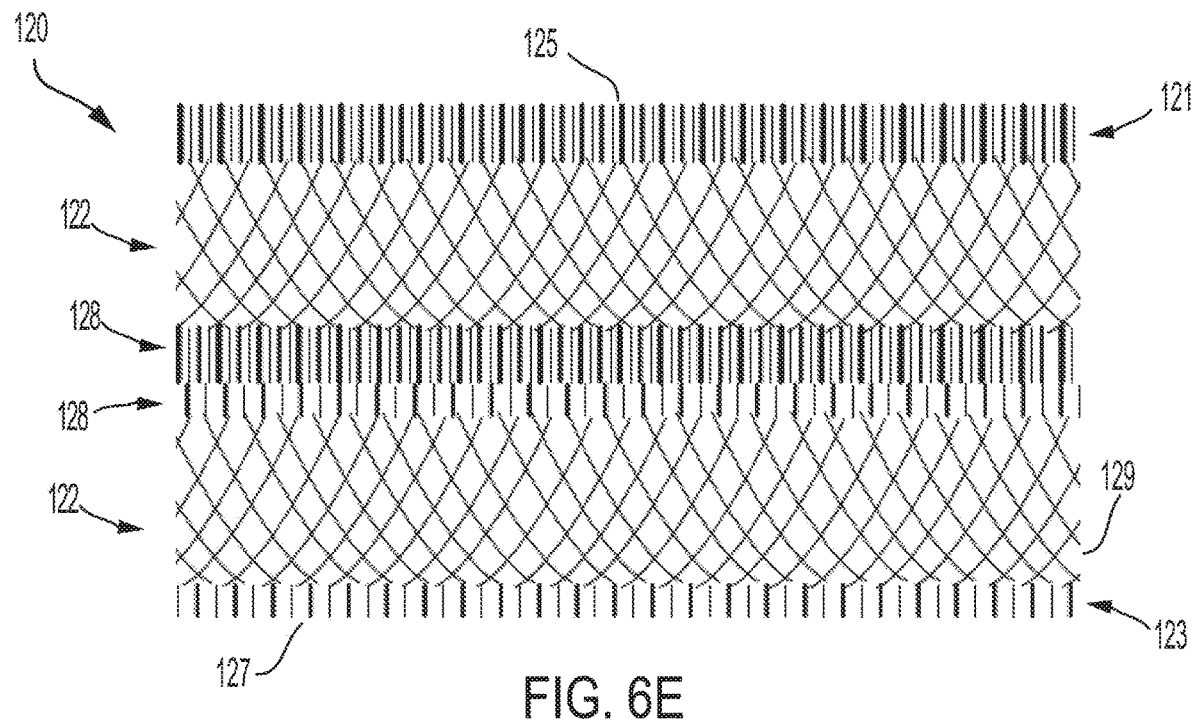
Figure 6F:
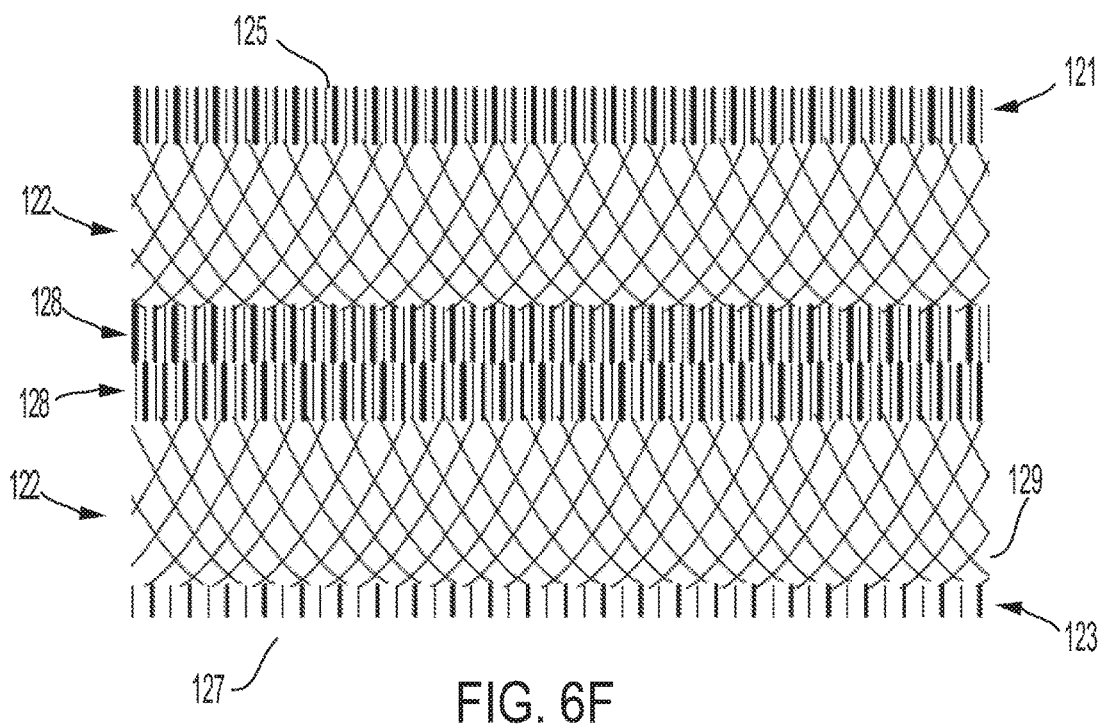

As representatively illustrated by the embodiments of FIGS. 6E and 6F, an increased thickness of the decompression layer 120 may be accomplished by incorporating one or more additional textile layers 128 (similar to the upper layer 121 or the lower layer 123) into the decompression layer 120 structure. As shown in FIGS. 6E and 6F, these additional one or more layers 128 may be integrated into the decompression layer 120 structure via one or more additional intermediate layers 122. To maximize the pulling force imparted by the decompression layer 120 onto the skin, the additional textile layer 128 are advantageously integrated into the decompression layer 120 in a manner that maintains the center of stiffness of the decompression layer 120 closer to the outwardly-facing surface 125. For example, as illustrated by the embodiment of FIG. 6E, the decompression layer 120 may comprise the decompression layer 120 of FIG. 6A bonded, or otherwise attached) along the outwardly-facing surface 125 of the decompression layer 120 of FIG. 6B. As shown in Table 7, such a multilayer decompression layer 120 configuration as illustrated by the embodiment of FIG. 6E may provide an increase in perfusion and flow at a treatment tissue site of 51.2% as compared to a decompression layer formed of a single layer, uniformly dense, reticulated foam material.

C. Interface Layer

An optional interface layer 130 (i.e. skin contact layer) is disposed adjacent the skin of the patient upon the attachment of the dressing 100 to the patient. The interface layer 130 may be incorporated into the dressing 100 for a variety of reasons, and may be defined by a variety of different features. For example, the interface layer 130 may be configured to: decrease discomfort and irritation during use of the treatment system 10; provide cooling; wick liquid away from the skin; function as an antimicrobial barrier; create friction between the decompression layer 120 and the skin to enhance the lifting force imparted onto the skin by the decompression layer 120, etc.

The materials forming the interface layer 130 may be selected based on the desired features of the interface layer 130. In general, the optional interface layer 130 is constructed from a light-weight, thin material that does not impede flow between the skin and the decompression layer 120, and which does not irritate the skin. As shown in FIG. 11A, in some embodiments, the interface layer 130 may comprise a textile, or other porous material, such as, e.g., a non-woven, breathable fabric. As shown in FIG. 3, in other embodiments, the interface layer 130 may be formed from an occlusive material including a plurality of perforation or holes formed therethrough. The interface layer 130 is optionally also formed having a durability and resilience sufficient to allow for reuse of the interface layer 130.

The interface layer 130 may be integrated into the dressing 100 according to a variety of arrangements. In some embodiments the interface layer 130 is provided entirely separate and detached from the decompression layer 120. In some such embodiments, the interface layer 130 may be provided as a sock or sleeve that is slid onto and around a treatment tissue site (e.g., a leg or arm of the patient). Once positioned in the desired location, the decompression layer 120 and occlusive layer 110 components of the dressing 100 are attached to the patient. Such a decoupled arrangement may advantageously allow a user to verify that the interface layer 130 lies taut and smoothly along the skin prior to attaching the remaining components of the dressing 100, thus minimizing the risk of pinching resulting from wrinkling along the interface layer 130 during use of the treatment system 10.

Figure 8A:
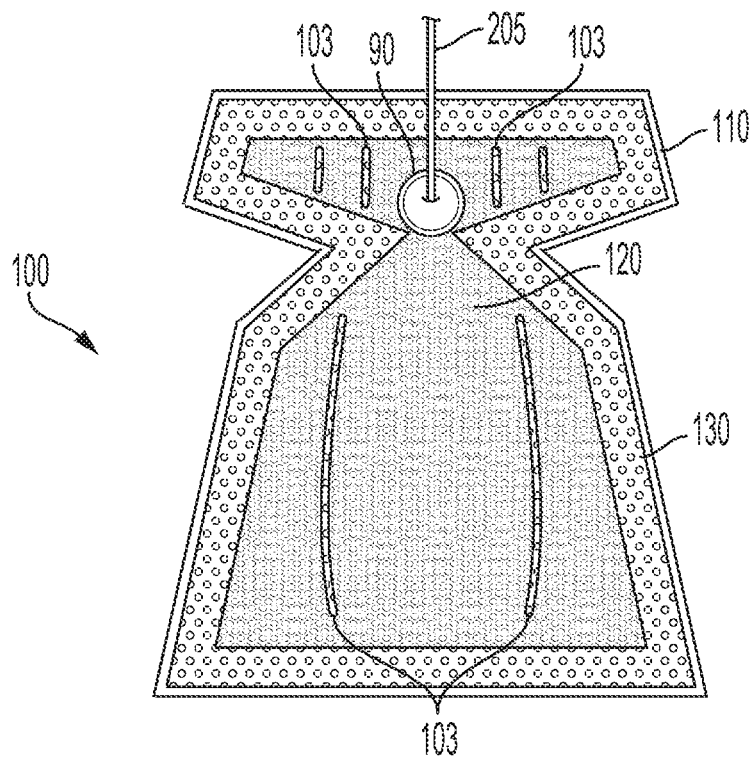
FIG. 8A is a perspective view of a dressing of a decompression treatment system, according to an illustrative embodiment.

Alternatively, the interface layer 130 is partially, or entirely, attached along the tissue-facing surface 127 of the decompression layer 120, such as, e.g., illustrated by the embodiment of FIG. 8A. In some embodiments, the interface layer 130 is removably attached to the decompression layer 120, allowing the interface layer 130 to be detached as desired (e.g., to wash the interface layer 130 prior to reuse of the treatment system 10). In other embodiments, the interface layer 130 is instead be fixedly secured to the entirety of, or a portion of (e.g., the peripheral edges of) a lower surface of the decompression layer 120 (e.g., by heat bonding, via adhesive, via ultrasonic welding, etc.). Such a fixed attachment of the interface layer 130 and the decompression layer 120 may advantageously minimize the presence of loose spots between the interface layer 130 and decompression layer 120, which may reduce the occurrence of ridges and bubbling, and thereby minimize the risk of pinching during operation of the treatment system 10.

D. Seal Member

A seal member of the dressing 100 is used to provide a sealing (e.g., fluid-tight) attachment between the occlusive layer 110 and an underlying surface (e.g., skin, a section of the occlusive layer 110 that has been wrapped around the patient, an optional interface layer 130, etc.) that enables a vacuum to be created and maintained within the treatment chamber surrounding the tissue treatment site. Advantageously, the seal member is structured to be sufficiently robust to continuously, or intermittently, maintain a desired negative pressure within the treatment chamber over the duration of use of the treatment system 10. The seal member is advantageously self-adhering and is able to provide a fluid-tight attachment to a variety of different surfaces, including, e.g., skin, the optionally included interface layer 130, the decompression layer 120, the occlusive layer 110, etc. In embodiments in which the seal member is reusable, the seal member is advantageously sterilizeable. Alternatively, the seal member may be replaceable (e.g., removable), such that a new seal member may be used with each subsequent use of the treatment system 10.

The seal member may be defined by a variety of, and combination of, various sealing structures. As shown in FIG. 9B, the seal member may optionally comprise a discrete component(s) provided separately from the other components of the dressing 100. For example, the seal member may comprise a tape-like or film-like structure 141 (e.g., thermoplastic elastomer gel strips, silicone/acrylic trilaminate film, etc.) that is applied along the entirety of, or along the outer periphery of, the upper layer of the occlusive layer 110 to secure the dressing 100 to the patient. In other embodiments, the seal member alternatively, or additionally, includes a wiper seal 143 (see, e.g., FIG. 1), adhesive (e.g., an acrylic or silicone adhesive), or other sealing structure (e.g., a gasket) that is provided along (e.g., integrated with) or disposed between, an entirety or periphery of a lower surface of the occlusive layer 110.

In various embodiments, the sealing attachment provided by the seal member may be reinforced and/or concealed by a hook-and-pile fastener, cohesive bandage, cast protector, or other structure that is positioned atop the dressing 100 following the attachment of the dressing 100 to a patient.

Dressing Configurations

The size, shape and configuration of the dressing 100 may vary depending on a variety of factors, including, e.g., the treatment tissue site being treated, the patient being treated, the duration of the treatment being provided, etc. Additional features of the dressing 100 that may be varied depending on the desired use of the treatment system 10 include, e.g., the degree of tailoring of the dressing 100 to a particular treatment site, the extent to which the dressing 100 is attached to a patient, the incorporation of features facilitating the attachment of the dressing 100 to a patient, the degree of integration of the components of the dressing 100, etc.

Figure 9A:
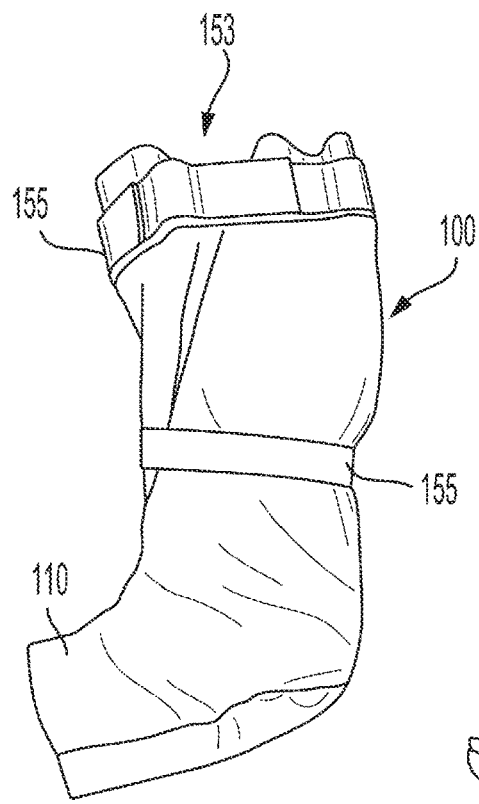
FIG. 9A is a perspective view of a dressing of a decompression treatment system, according to an illustrative embodiment.
Figure 9B:
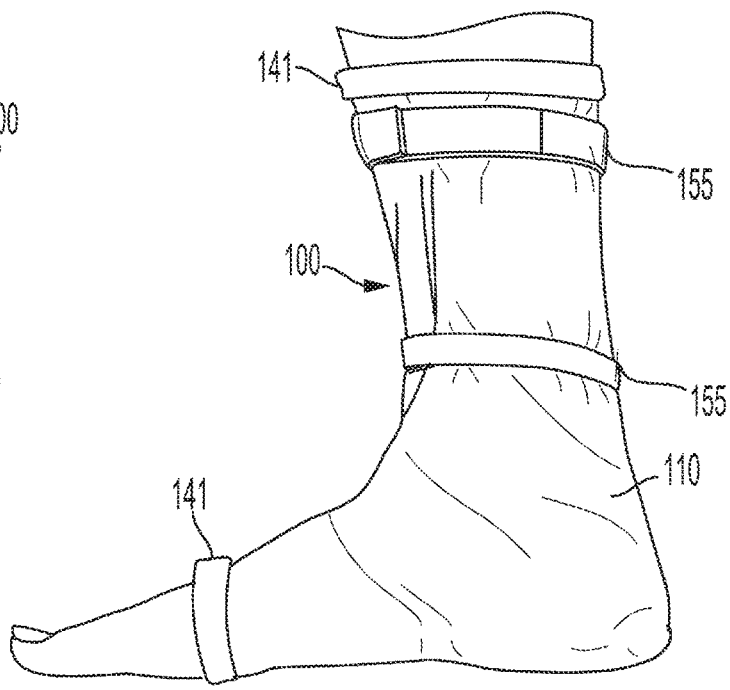
FIG. 9B is a perspective view of the dressing of FIG. 9A attached to a patient, according to an illustrative embodiment.
Figure 10:
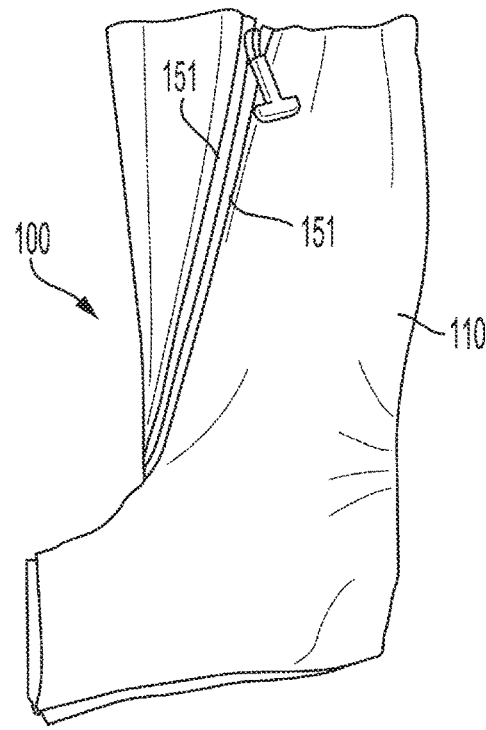
FIG. 10 is a perspective view of a dressing of a decompression treatment system, according to an illustrative embodiment.

As illustrated in FIGS. 9A and 10, according to various embodiments the dressing 100 defines a closed annular structure configured to extend circumferentially about an entirety of a limb or other extremity by at least 360°. Upon attachment, the dressing 100 partially, or entirely, envelops the extremity.

In some embodiments, the annular dressing 100 is defined by a sleeve-like structure having a generally tubular shape that extends between a first open end and a second open end. In other embodiments the sleeve-like annular dressing 100 extends between a first open end and a second open end, and is shaped, sized and contoured for attachment around a specific extremity of a patient. For example, referring to FIGS. 9A and 10, in some embodiments the dressing 100 defines an open-toe boot structure configured to receive a foot. In other embodiments, the annular dressing 100 defines a receiving portion that is configured to receive a portion (or the entirety) of an extremity of a user (e.g., a hand, afoot, a stump, etc.). The receiving portion is accessible via a single open end defined by the annular dressing 100. The receiving portion defined by the annular dressing 100 may be generally cylindrical in shape, or may optionally define a structure that is shape, size and contoured to receive a specific extremity of a patient. For example, the dressing 100 may comprise a glove or mitten structure for receiving a hand of a patient, or may comprise a sock, or closed-toe boot structure for receiving a foot of a patient. Such customization of the dressing 100 to a specific treatment tissue site may advantageously facilitate an air-tight attachment of the dressing 100 to the treatment tissue site. The annularly extending dressing 100 optionally includes folds and/or other articulation features configured to allow for at least a partial degree of flexion or movement during treatment using the therapy system.

In embodiments in which the dressing 100 is defined by an annularly extending structure having one open end or two open ends, and which is configured to encircle or otherwise circumscribe a portion of the patient, the dressing 100 may be formed from materials that allow the dressing 100 to stretch during application of the dressing 100 around a patient. Alternatively, or additionally, the dressing 100 optionally includes one or more features configured to facilitate the application of the dressing 100 around the patient. For example, as illustrated in FIG. 10, the dressing 100 optionally includes a slit extending partially, or entirely, along a length thereof. Mating engagement elements 151 (e.g., mating zipper teeth, hook and pile, etc.) are optionally provided along the length of each edge defining the slit to allow the edges to be selectively coupled and decoupled from one another. In some such embodiments, one or both of the edges optionally comprises a plurality of similar or identical engagement elements that are spaced generally parallel to each other at one or more locations spaced inwardly from the edge, thus allowing the diameter of the dressing 100 to be adjusted as needed.

As an alternative to (or in addition to) constricting the dressing 100 from materials that provide for a degree of stretch and/or the inclusion of a slit such as representatively illustrated in FIGS. 9A and 9B, the dressing 100 in some embodiments includes a gusset 153 that may be let out (or taken in) via the tightening of an annularly extending strap 155 (e.g., mating hook-and-pile straps, etc.) to increase (or decrease) the dimensions of the opening of the dressing 100. In yet other embodiment, the components of an annularly-shaped dressing 100 are optionally also (or alternatively) formed from elastic materials that allow the dressing 100 to stretch and expand to facilitate the insertion of a limb or other extremity into the opening of the dressing 100 during the attachment of the dressing 100 to a patient.

According to other embodiments, the dressing 100 may alternatively be defined by a flexible, sheet-like structure. The sheet-like dressing 100 may be provided in a range of shapes and sizes. As representatively illustrated by the embodiment of FIG. 3, in some embodiments the sheet-like dressing 100 is optionally shaped and sized for application to a particular treatment site.

Figure 8B:
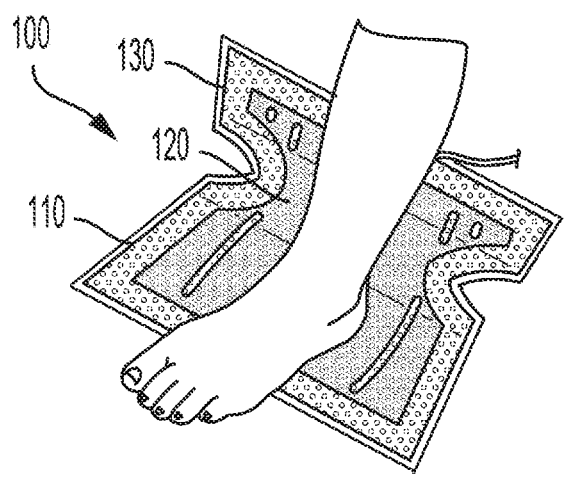
FIG. 8B is a perspective view of the dressing of FIG. 8A being attached to a patient, according to an illustrative embodiment.
Figure 8C:
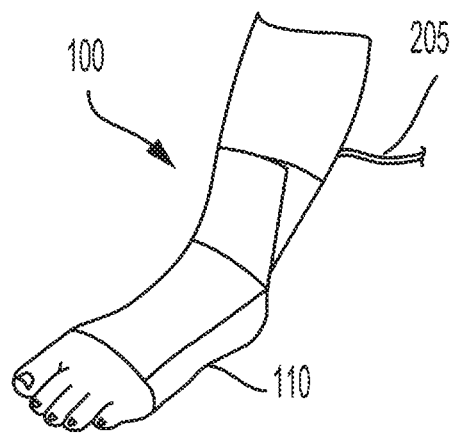
FIG. 8C is a perspective view of the dressing of FIG. 8A attached to a patient, according to an illustrative embodiment.

As illustrated in FIGS. 8A and 8B, in some embodiments, a sheet-like dressing 100 may be wrapped around a treatment tissue site to substantially (e.g. entirely) circumscribe a portion of the patient (e.g. a calf, a wrist, an ankle, etc.). For example, the sheet-like dressing 100 may be configured to be wrapped around a limb or extremity of a patient by approximately 360° or more. Alternatively, as shown in FIGS. 11A and 11B, in other embodiments, the sheet-like structure defining the dressing 100 is attached to a patient as a patch, in which the outer periphery of the sheet-like dressing 100 circumscribes the treatment tissue site, but does not circumscribe the limb or extremity of the patient along with the treatment tissue site is located (e.g., the dressing 100 may extend less than 360° around a limb or extremity, such as e.g., when the dressing 100 is applied over a knee or shoulder). In some such embodiments, (and/or in other dressing 100 embodiments), the dressing 100 is optionally provided with a thin, semi-rigid, pliable (e.g. bendable, shapeable, etc.) reinforcement layer that allows the sheet-like dressing 100 to be adapted to match the contours of the treatment tissue site to which the dressing 100 is to be attached, thereby facilitating the attachment of the dressing 100 to the patient. As shown in FIGS. 11A and 11B, the sheet-like dressing 100 optionally includes folds and/or other articulation features 103 configured to allow for at least a partial degree of flexion or movement during treatment using the therapy system.

According to yet other embodiments, the dressing 100 may be provided as a flexible tape that can be wound around a treatment tissue site, or which may be attached as one or more strips atop a treatment tissue site. Such a tape-like dressing 100 arrangement may provide a user with the ability to customize the attachment of the treatment system 10 to a variety of different treatment sites and to a variety of different patients. In some embodiments, an adhesive is optionally provided along an outer periphery of the tape-like structure to facilitate the attachment of the dressing 100 to the patient. In such embodiments, the application of the tape-like structure such that adjacent segments of the tape (e.g. adjacent winding or adjacent strips) overlap may allow the dressing 100 to be attached to a patient without requiring any additional sealing of the dressing 100 to the patient. Alternatively, an additional sealing layer (such as, e.g., the occlusive layer 110) may be attached to a patient to surround the tape-like dressing 100 that has been applied to the patient.

The various to dressing 100 configurations and features described above may apply to all of, or only some of, the components of the dressing 100. For example, as representatively illustrated by the embodiment of FIG. 1, in some embodiments, the occlusive layer 110 and the interface layer 130 may be defined by annular structures configured to be slid onto a foot of the patient, while the decompression layer 120 comprises a tape-like structure that may be wound around the occlusive layer 110 prior to the attachment of the occlusive layer 110.

Configuration of Exemplary Embodiments

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

What is claimed is:

1. An apparatus for applying a lifting force to a tissue site of a patient, the apparatus comprising: an occlusive layer configured to be sealed to the patient around the tissue site to define a chamber; a decompression layer disposed within the chamber defined by the occlusive layer at a location proximate the tissue site, the decompression layer a compressible fabric defining one or more channels therethrough; and a connector provided along the occlusive layer, the connector configured to fluidly couple the chamber to a vacuum source; wherein, the decompression layer comprises a center of stiffness located closer to an upper surface of the decompression layer facing away from the tissue site than to a lower surface of the decompression layer facing the tissue site such that upon operation of the vacuum source, the decompression layer is configured to compress in a direction away from the tissue site, and wherein the center of stiffness is not provided by a coating stiffener.

2. The apparatus of claim 1, wherein the decompression layer comprises a macro-mesh material.

3. The apparatus of claim 2, wherein the macro-mesh material includes:
   an upper layer;
   a lower layer; and
   a plurality of filaments extending between and connecting the upper layer and the lower layer.

4. The apparatus of claim 3, wherein the upper layer has a higher stiffness than the lower layer.

5. The apparatus of claim 4, wherein the macro-mesh material further comprises a first intermediate layer disposed between the upper layer and the lower layer, the first intermediate layer having a higher stiffness than the lower layer.

6. The apparatus of claim 3, wherein the filaments are flexible, such that a distance between the upper layer and the lower layer prior to operation of the vacuum source is greater than a distance between the upper layer and the lower layer during operation of the vacuum source.

7. The apparatus of claim 1, further comprising an interface layer located below the lower surface of the decompression layer, the interface layer configured to contact skin surrounding the tissue site upon sealing of the occlusive layer to the patient.

8. The apparatus of claim 7, wherein the interface layer is a discrete structure provided separately from the decompression layer.

9. The apparatus of claim 8, wherein the interface layer is selectively releasably attached to at least one of the decompression layer and the occlusive layer.

10. The apparatus of claim 1, wherein the occlusive layer and decompression layer are attached to one another to define an annular structure comprising at least a first open end, the annular structure being sized for attachment, to one of a knee, ankle, leg, arm or hand of the patient.

11. The apparatus of claim 10, the annular structure defining a sleeve-shaped structure that further comprises a second open end.

12. The apparatus of claim 1, wherein the occlusive layer is configured to extend at least 360° around an extremity defining the tissue site upon being sealed to the patient, and the decompression layer is configured to compress in a radially outwards direction during operation of the vacuum source.

13. The apparatus of claim 1, wherein a center of mass of the decompression layer is located at a height along the decompression layer that is closer to the upper surface of the decompression layer than to the lower surface of the decompression layer.

14. A method for providing decompression therapy, comprising: attaching a dressing proximate intact skin extending over a treatment site, wherein the dressing comprises: an occlusive layer configured to define a chamber between the skin of a patient and a lower surface of the occlusive layer, and a compressible decompression layer a plurality of fluid channels extending therethrough, wherein the compressible decompression layer comprises a center of stiffness located closer to an upper surface of the decompression layer facing away from the treatment site than to a lower surface of the decompression layer facing the treatment site, and wherein the center of stiffness is not provided by a coating stiffener; and evacuating air from the chamber;
   wherein the evacuation of air from the chamber causes the decompression layer to compress in a direction away from the treatment site.

15. The method of claim 14, further comprising attaching an interface layer proximate the intact skin extending over the treatment site.

16. The method of claim 15, wherein attaching the occlusive layer and decompression layer occurs after attaching the interface layer to the skin of the patient.

17. The method of claim 14, wherein the treatment site is a location corresponding to at least one of a broken bone in a limb, a sprained tissue and a strained tissue, and wherein the evacuation of air from the chamber reduces swelling at the treatment site from a first degree of swelling to a second degree of swelling.

18. The method of claim 17, wherein the treatment site undergoes surgical treatment following the reduction of swelling at the treatment site from the first degree of swelling to a degree of swelling that is equal to, or less than, the second degree of swelling, the reduction of swelling from the first degree of swelling to the second degree of swelling occurring from 3 to 7 days following an initial operation of the air displacement device to evacuate air from the chamber.

19. The method of claim 14, wherein compression of the decompression layer in a direction away from the treatment site is configured to pull the intact skin in a direction outward relative to the treatment site.

20. An apparatus for increasing at least one of blood perfusion and lymphatic flow at a tissue site, the apparatus comprising: a circumferentially extending occlusive layer configured to be sealed to a patient around the tissue site to define a chamber; a decompression layer having a lower surface configured to be disposed proximate the tissue site within the chamber defined by the occlusive layer; and a connector configured to fluidly couple the chamber to a vacuum source; wherein, the decompression layer comprises a center of stiffness located closer to an upper surface of the decompression layer facing away from the tissue site than to the lower surface of the decompression layer such that upon operation of the vacuum source, the decompression layer is configured to compress in a direction away from the tissue site, and wherein the center of stiffness is not provided by a coating stiffener.

21. The apparatus of claim 20, wherein the decompression layer comprises a first mesh layer vertically offset from a second mesh layer by a flexible layer, the first mesh layer being positioned opposite the occlusive layer and the second mesh layer being positioned opposite the tissue site.

22. The apparatus of claim 21, wherein the second mesh layer moves radially outwards towards the first mesh layer during operation of the vacuum source.

23. The apparatus of claim 20, wherein the occlusive layer comprises one of a boot-shaped or hand-shaped configuration.

24. The apparatus of claim 20, wherein a size of the decompression layer is smaller than a size of the occlusive layer, such that the decompression layer is concentric relative to the occlusive layer.

* * * * *